United States Patent
Warman et al.

[11] Patent Number: 5,968,079
[45] Date of Patent: Oct. 19, 1999

[54] METHOD AND APPARATUS FOR DIAGNOSIS AND TREATMENT OF ARRHYTHMIAS

[75] Inventors: Eduardo N. Warman, Maple Grove; Rahul Mehra, Stillwater, both of Minn.

[73] Assignee: Medtronic, Inc., Minneapolis, Minn.

[21] Appl. No.: 09/040,544

[22] Filed: Mar. 18, 1998

[51] Int. Cl.⁶ .................................................. A61N 1/368
[52] U.S. Cl. ........................................................... 607/5
[58] Field of Search .................................. 607/4, 5, 6, 7, 607/14

[56] References Cited

U.S. PATENT DOCUMENTS

| | | | |
|---|---|---|---|
| 5,507,780 | 4/1996 | Finch | 607/5 |
| 5,545,186 | 8/1996 | Olson et al. | 607/14 |
| 5,578,063 | 11/1996 | Bocek et al. | 607/5 |
| 5,755,736 | 5/1998 | Gillberg et al. | 607/4 |

*Primary Examiner*—Scott M. Getzow
*Attorney, Agent, or Firm*—Reed A. Duthler; Harold R. Patton

[57] ABSTRACT

An implantable medical device which senses atrial electrograms, detects atrial tachyarrhythmias and delivers atrial cardioversion/defibrillation pulses in response thereto, which employ a correlation analysis to assist in detection of arrhythmias and/or timing of delivery of cardioversion/defibrillation shocks. The device includes an electrogram recorder which stores atrial electrogram segments associated with R—R intervals extending over multiple atrial depolarizations and a correlator which measures correlation of successive stored atrial electrogram segments. The device may use the measured corellation meeting a defined threshold value to detect the occurrence of a defined tachyarrhythmia such as atrial fibrillation or allow delivery of a cardioversion/defibrillation pulse.

10 Claims, 6 Drawing Sheets

METHOD AND APPARATUS FOR DIAGNOSIS AND TREATMENT OF ARRHYTHMIAS

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/ defibrillators relied upon the presence or absence of electrical and mechanical heart activity (such as intra-myocardial pressure, blood pressure, impedance, stroke volume or heart movement) and/or the rate of the electrocardiogram to detect hemodynamically compromising ventricular tachycardia or fibrillation. Presently available pacemaker/cardioverter/defibrillator arrhythmia control devices, such as the Model 7219 and Model 7221 implantable pacemaker/cardioverters/defibrillators commercially available from Medtronic, Inc., employ programmable fibrillation interval ranges and tachycardia detection interval ranges, along with measurement of suddenness of onset and rate variability.

For future generations of devices, numerous detection and classification systems have been proposed. Numerous patents, including U.S. Pat. No. 5,217,021 issued to Steinhaus et al., U.S. Pat. No. 5,086,772 issued to Lanard et al., U.S. Pat. No. 5,058,599 issued to Andersen and U.S. Pat. No. 5,312,441 issued to Mader et al propose waveform morphology analysis systems for determining the type and origin of detected arrhythmias. Other patents, including U.S. Pat. No. 5,205,583 issued to Olson, U.S. Pat. No. 5,913,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al. propose systems for analysis of order and timing of atrial and ventricular events. Complex dual chamber detection mechanisms which rely upon a sets of ordered rules which are applied to distinguish between various atrial and ventricular arrhythmias are disclosed in U.S. Pat. No. 5,545,186, issued to Olson et al. and in pending U.S. application Ser. No. 08/895,342, filed on Jul. 17, 1997 by Gillberg et al. for a "Prioritized Rule Based Method and Apparatus for Diagnosis and Treatment of Arrhythmias .

In spite of the extensive work done toward optimizing detection methodologies, there are still situations in which improvements in detection methodology are to be desired. One such situation is the detection and classification of rhythms which may be due to atrial fibrillation and/or atrial flutter. In some cases, these two rhythms are difficult to distinguish, and in other cases, the patient may move between the two types of rhythm, during either the detection process or during the process of delivering an electrical therapy to terminate the rhythm.

SUMMARY OF THE INVENTION

The present invention is directed to a mechanism for detecting and distinguishing between atrial fibrillation and atrial flutter which may be employed to more accurately select and deliver the therapy to treat the detected arrhythmias.

The present invention accomplishes these goals by means of morphological analysis of the electrogram signal taken from the heart, preferably taken between two large surface area electrodes adjacent the atrium, for example between superior vena cava and coronary sinus defibrillation electrodes. The electrogram sensed between these electrodes is digitized and stored. The occurrence of R waves is monitored and the stored electrogram is divided into segments associated with successive R—R intervals. On a sensed R wave, the stored electrogram associated with the R—R interval ending on the sensed R wave is compared to the electrogram associated with the preceding R—R interval to determine the degree of correlation of the two stored electrogram segments.

The stored segments employed in conjunction with the invention need not include the entire electrogram signal between the R-waves which begin and end the R—R interval, but may only extend for a defined length of time, for example for a time period corresponding to two or three of the average intervals separating atrial depolarizations or for a similar pre-set time period. The stored segment for an R—R interval may begin with the R-wave initiating the R—R interval or may begin after a delay following the R-wave. Each electrogram segment will preferably include multiple atrial depolarizations and may also reflect to some degree the far-field R waves as sensed by the electrodes adjacent the atrium. Preferably, the stored electrogram segments are shifted relative to one another up to a defined maximum, for example, up to one average interval between atrial depolarizations, until a maximum correlation value for the overlapping portions of the electrogram segments is achieved.

Shifting of the stored electrogram segments may be accomplished, for example by comparing two successively stored electrogram segments of equal length (e.g. three average A—A intervals) to one another by shifting one segment relative to the other until a maximum corellation is achieved between the overlapping portions of the stored segments, subject to the limitation that the overlapping portions of the stored electrogram segments must extend for a predefined period, (e.g. two average A—A intervals). Alternatively, for each comparison of two successive stored electrogram segments, either the earlier or the later of the stored segments may be truncated to provide a stored electrogram segment of a shorter duration (e.g. shortened from three average A—A intervals to two average A—A intervals) and the shorter stored segment shifted relative to the longer stored segment to a position of maximum corellation, subject to the constraint that the shorter stored segment completely overlaps the longer stored segment.

If the maximum correlation value in the area of overlap of the compared segments exceeds a preset value, for example, 90%, the device determines that the atrial rhythm presently under way is either a relatively highly organized form of atrial fibrillation or is atrial flutter. This information may be employed by the device, both in conjunction with detection and classification of the arrhythmia to be treated by the device, and in conjunction with a determination of the appropriate time to deliver therapy to treat the detected arrhythmia.

In its first application of the invention, the device employs the measurement of correlation between the electrograms associated with successive R—R intervals in conjunction with other detection methodologies intended to detect the presence of a high rate atrial tachyarrhythmias such as atrial fibrillation or atrial flutter. In this aspect of the invention, the correlation measurement is used to distinguish between atrial fibrillation and atrial flutter for purposes of selecting between differing therapies for each of the arrhythmias. For example, in the case of atrial fibrillation, a scheduled sequence of therapies may be defined which consists of successively increasing amplitude cardioversion or defibrillation pulses to be applied to the atrium, while in the case of atrial flutter, the therapies provided may consist of a set of therapies beginning with high frequency burst pacing, and proceeding to include gradually increasing high voltage cardioversion pulses at lower levels than would be provided to treat atrial fibrillation. In this aspect of the invention, the correlation analysis may be applied over a sequence of R—R intervals in response to preliminary detection of a high rate atrial tachyarrhythmia, with the requirement that the correlation measured over a defined number of successive R—R intervals be above a defined value in order to determine that the arrhythmia present is atrial flutter, rather than atrial fibrillation.

In the second application of the invention, the correlation measurement may be employed in order to determine the timing of the delivery of a therapy in response to detection of atrial fibrillation. In this aspect of the invention, after detection of atrial fibrillation or of a high rate atrial arrhythmia at a rate consistent with atrial defibrillation, the device may charge its output capacitors in preparation to deliver an atrial defibrillation pulse. Thereafter, the correlation analysis may be applied over a defined time period repeatedly until such time as the electrogram segments associated with two successive R—R intervals exhibit a correlation percentage greater than a predefined value. At such time as the required degree of correlation is detected, the device may schedule an atrial cardioversion or defibrillation pulse synchronized to the next successive R wave. In this aspect of the invention, the device may be able to successfully cardiovert or defibrillate high rate atrial tachyarrhythmias at a lower amplitude than might be possible using more traditional synchronization algorithms, due to the relatively more organized nature of the arrhythmia at the point at which the shock is delivered. In some patients, this is believed to provide the opportunity to successfully terminate a detected high rate atrial tachyarrhythmia quickly, with a lower level of pain associated with the pulse than might otherwise be possible.

In a further aspect of the second application of the invention, detection of a more organized atrial rhythm consistent with the electrogram segments exhibiting a high degree of correlation may also be used to select a different treatment than originally selected. For example, in response to the electrogram segments associated with two successive R—R intervals exhibiting the desired degree of correlation, the therapy may be altered from the scheduled atrial defibrillation pulse to a high frequency burst, pacing level pulse therapy. It is believed that in some patients this implementation of the invention will allow termination of high rate tachyarrhythmias in some cases using pacing pulse level therapies which would otherwise require delivery of high amplitude cardioversion or defibrillation shocks. In this application of the invention, it may be employed both to control timing of the delivery of an atrial defibrillation therapy and to provide the opportunity to deliver a less aggressive therapy in the presence of a more highly organized rhythm.

DETAILED DESCRIPTION OF THE PREFERRED EMBODIMENTS

Figure 1:
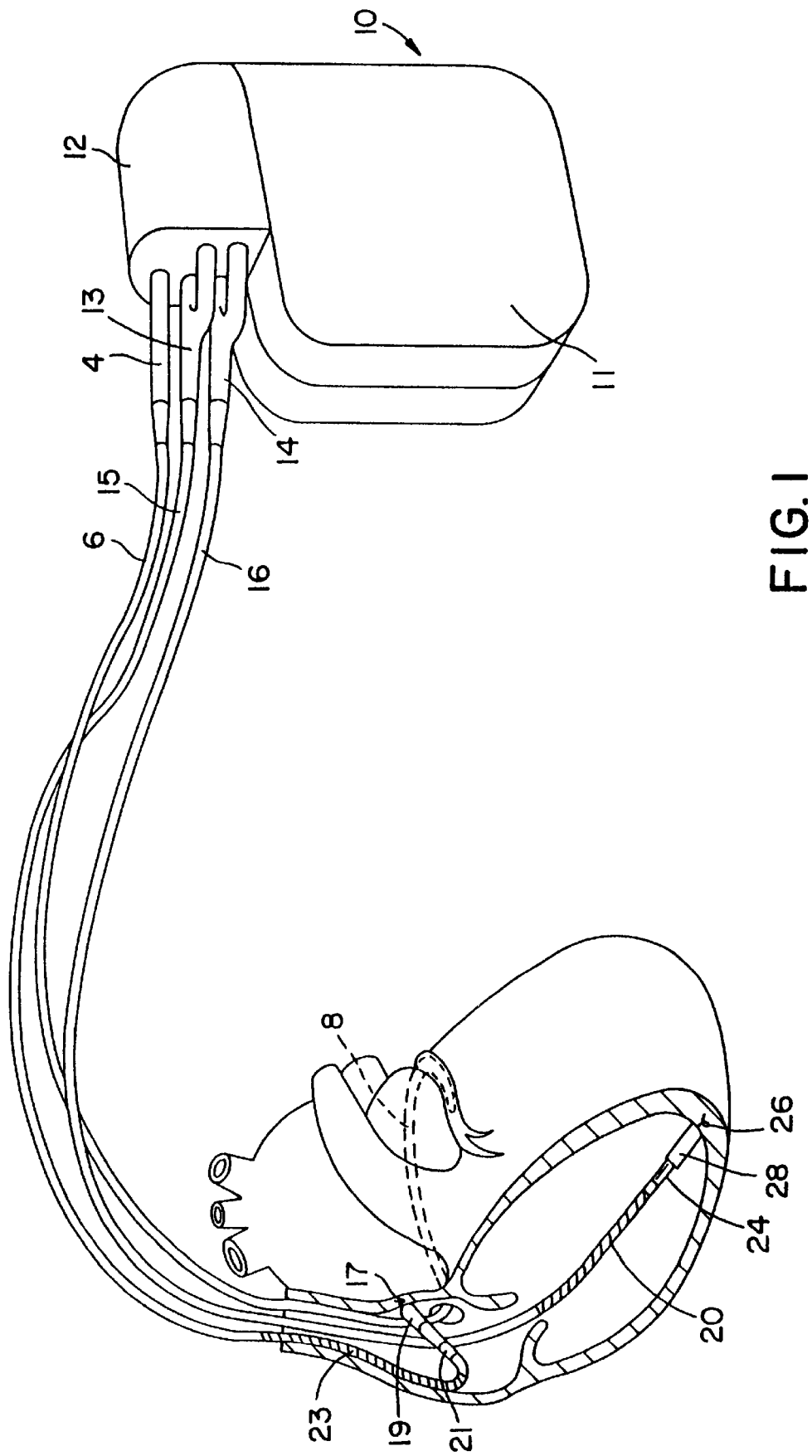
FIG. 1 illustrates a first embodiment of an implantable pacemaker/cardioverter/ defibrillator of a type appropriate for use in practicing the present invention, in conjunction with a human heart.

FIG. 1 illustrates a defibrillator and lead set according to the present invention. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three mutually insulated conductors, corresponding generally to the structure of the ventricular lead. Located adjacent the J-shaped distal end of the lead are a ring electrode 21 and an extendable helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is about 10 cm in length or greater and is configured to extend from the SVC toward the tricuspid valve. At the proximal end of the lead is a bifurcated connector 13 which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may op course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
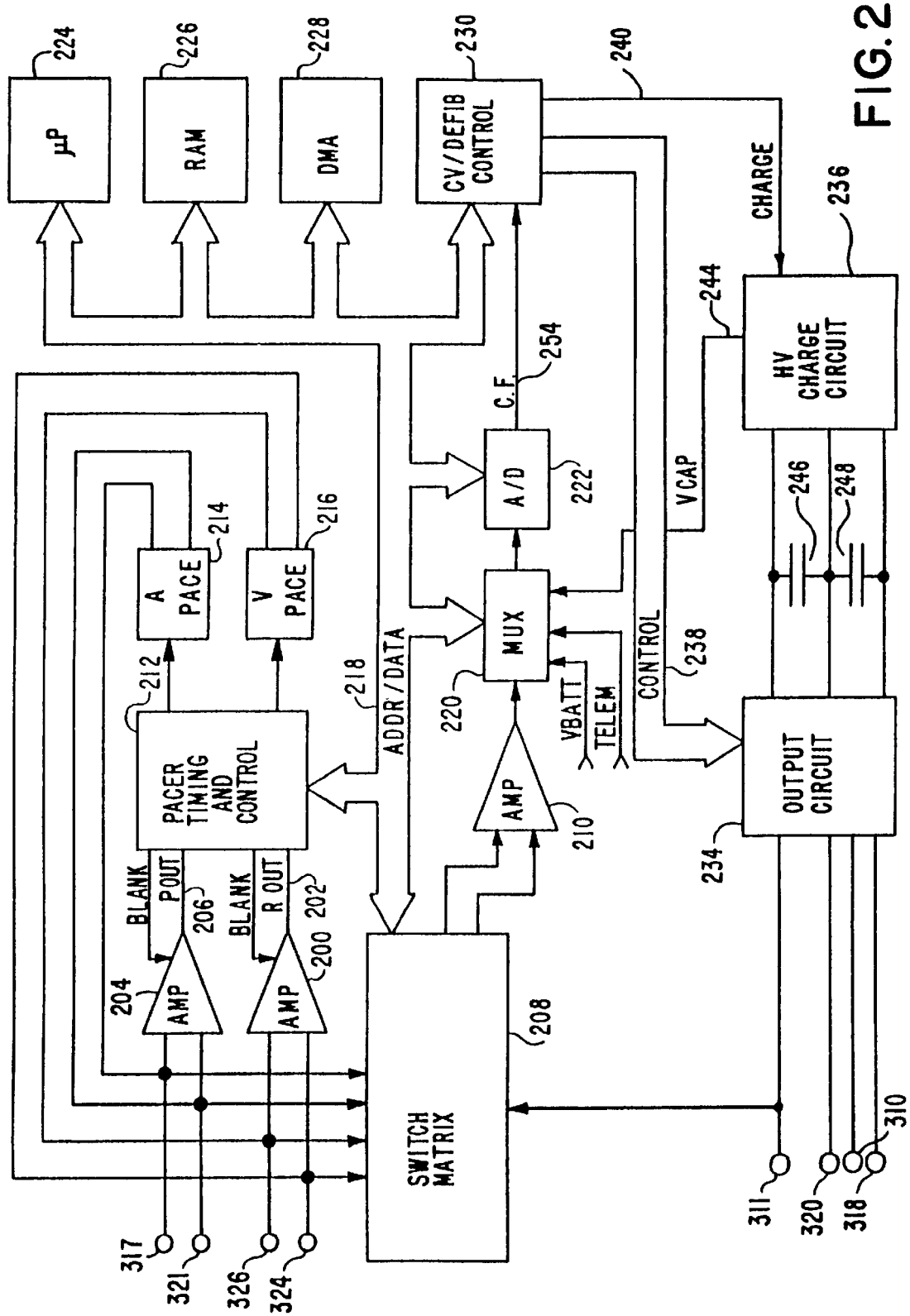
FIG. 2 illustrates a functional schematic diagram of an implantable pacemaker/cardioverter/ defibrillator in which the invention may be practiced.

FIG. 2 is a functional schematic diagram of an implantable pacemaker/cardioverter/ defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide antitachycardia pacing therapies, antitachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/ defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204. which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/ control circuitry 212 corresponding to the occurrences of sensed P-waves and R-waves and corresponding to the generation of cardiac pacing pulses. These interrupts are provided via data/address bus 218. Any necessary mathematical calculations to be per-formed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

In conjunction with the present invention, the microprocessor may employ any of a number of existing detection methodologies in order to detect and classify atrial and ventricular tachyarrhythmias. In particular, the present invention is believed to be particularly useful in conjunction with a device as described in copending U.S. patent application Ser. No. 08/895,342, filed by Gillbert et al for a "Prioritized Rule Based Method and Apparatus for Diagnosis and Treatment of Arrhythmias". However, the invention may also be practiced in conjunction with devices as disclosed in U.S. Pat. No. 5,549,641 issued to Ayers et al., U.S. Pat. No. 5,486,199 issued to Kim et al., U.S. Pat. No. 5,490,862 issued to Adams et al., U.S. Pat. No. 5,464,431 issued to Adams et al., U.S. Pat. No. 5,591,215 issued to Greenhut et al., U.S. Pat. No. 5,605,159 issued to Smith et al. and U.S. Pat. No. 5,545,186 issued to Olson et al., all incorporated herein by reference in their entireties. In conjunction with the present invention, microprocessor 224, under control of programming stored in a read only memory within microprocessor 224 will process the stored atrial and ventricular events and associated interval separating them in order to identify the occurrence of tachyarrhythmias and preferably to determine the origin of the tachyarrhythmias. In the context of the present invention, it is only necessary that the microprocessor 224 be able to identify the occurrence of a high rate atrial tachyarrhythmia. However, practical implementation of the device is believed that, as described above, the device will also include the ability to identify and treat ventricular tachyarrhythmias.

The random access memory 226 also serves as the location for storage of sensed and digitized electrogram segments to be employed in conjunction with the correlation function described above. After activation of the correlation function, the electrogram sensed between electrodes 318 and 310, corresponding to electrodes 23 and 8 in FIG. 1, passes through switch matrix 208, wide band amplifier 210, multiplexer 220 and is digitized by A-D converter 222 and provided to Address /Data Bus 218. The digitized electrogram is stored in random access memory 226 under control of direct memory circuitry 228. Ventricular depolarization is sensed between electrodes 326 and 324, corresponding to electrodes 24 and 26 in FIG. 1 define the beginning and end points of the stored electrogram segments corresponding to the R—R intervals stored in random access memory 226. These stored electrogram segments are compared with one another by microprocessor 224 to determine the correlation between the two signals. As noted above, the stored electrogram segments are preferably shifted with respect to one another up to one half of the average interval separating sensed atrial depolarizations or "P waves", until a maximum correlation is obtained. The value of this maximum correlation is stored in random access memory 226 for use by microprocessor 224 in determining the nature of the detected tachyarrhythmia and/or the nature of the therapy delivered and/or the timing of the therapy to be delivered, as discussed in more detail below.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Patent Application No. WO92/18198 by Adams et al., published Oct. 29, 1992, and in U.S. Pat. No. 4,316,472 by Mirowski et al., issued Feb. 23, 1982, both incorporated herein by reference in their entireties. In addition, high frequency pulse bursts may be delivered to electrodes 317 and 321 to terminate atrial tachyarrhythmias, as described in PCT Patent Publication No.

WO95/28987, filed by Duffin et al and PCT Patent Publication No. WO95/28988, filed by Mehra et al, both incorporated herein by reference in their entireties.

However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modem implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/ cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3B:
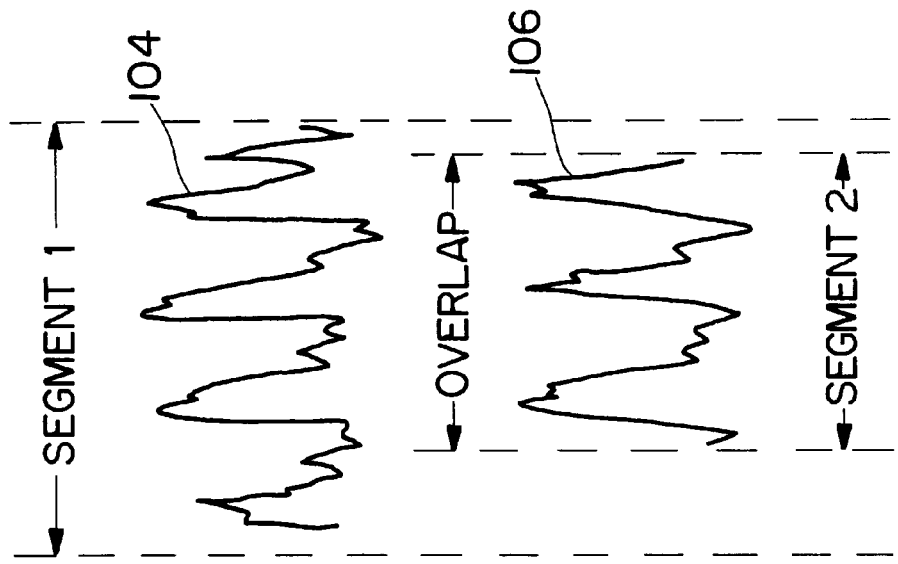
FIGS. 3A and 3B are sets of electrogram tracings illustrating the correlation function performed by the present invention.
Figure 3A:
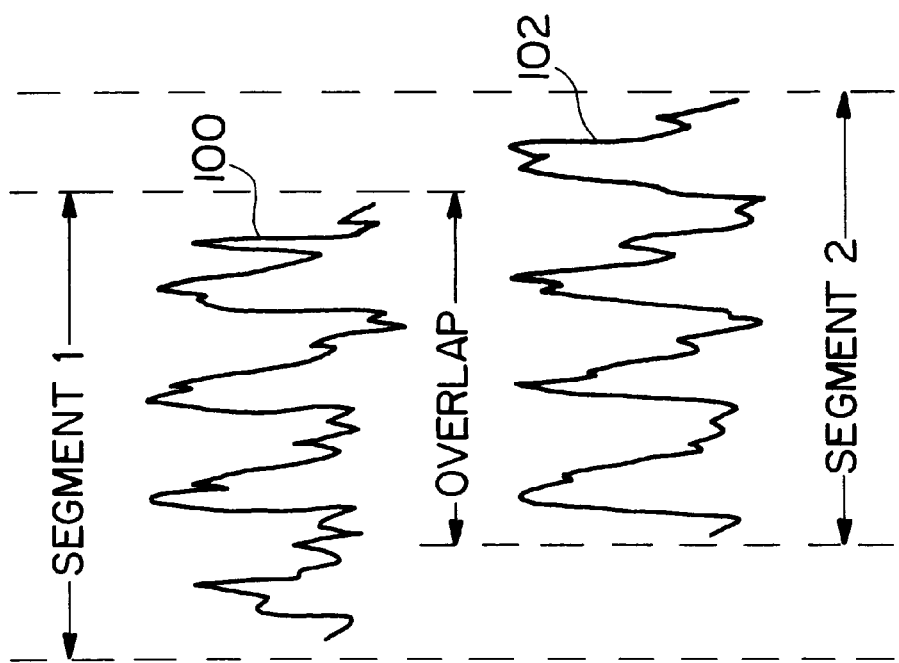

FIGS. 3A and 3B illustrate the correlation analysis function of the present invention. On a sensed R wave, the stored electrogram associated with the R—R interval ending on the sensed R wave is compared to the electrogram associated with the preceding R—R interval to determine the degree of correlation of the two stored electrogram segments as illustrated in FIG. 3A or FIG. 3B.

The stored segments employed in conjunction with the invention as illustrated do not include the entire electrogram signal between the R-waves which begin and end the R—R interval, but only extend for a defined length of time. In the case illustrated in FIG. 3A, the electrogram segments 100 and 102 each extend over a period of four average A—A intervals, which period can be employed in the presence of relatively low ventricular rates. For higher ventricular rates, shorter stored electrogram segments, for example extending for a time period corresponding to two or three average A—A intervals would be employed. In a preferred embodiment, the duration of the stored electrogram segments may vary automatically under control of the microprocessor 224 (FIG. 2) as a function of sensed ventricular rate. The stored segment for an R—R interval may begin with the R-wave initiating the R—R interval or may begin after a delay following the R-wave. As illustrated the stored electrogram segments 100 and 102 are shifted relative to one another until a maximum correlation value for the overlapping portions of the electrogram segments is achieved, subject to the limitation that the overlapping portions of the stored electrogram segments must extend for a predefined period, (e.g. two or three average A—A intervals).

FIG. 3B illustrates an alternative embodiment of the correlation analysis function of the present invention. In this embodiment one of the stored electrogram segments 106, which may be either the earlier or the later of the stored segments is truncated to provide a stored electrogram segment of a shorter duration, as illustrated shortened from four average A—A intervals to three average A—A intervals. The shorter stored segment 106 is shifted relative to the longer stored segment 104 to a position of maximum corellation, subject to the constraint that the shorter stored segment 106 completely overlaps the longer stored segment 104. If either of the two R—R intervals is less than the required number of A—A intervals, no corellation analysis will be done.

If the maximum correlation value in the area of overlap of the compared segments exceeds a preset value, for example, 90%, the device determines that the atrial rhythm presently under way is either a relatively highly organized form of atrial fibrillation or is atrial flutter as discussed above. This information may be employed by the device, both in conjunction with detection and classification of the arrhythmia to be treated by the device, and in conjunction with a determination of the appropriate time to deliver therapy to treat the detected arrhythmia, as discussed in more detail below.

Figure 4:
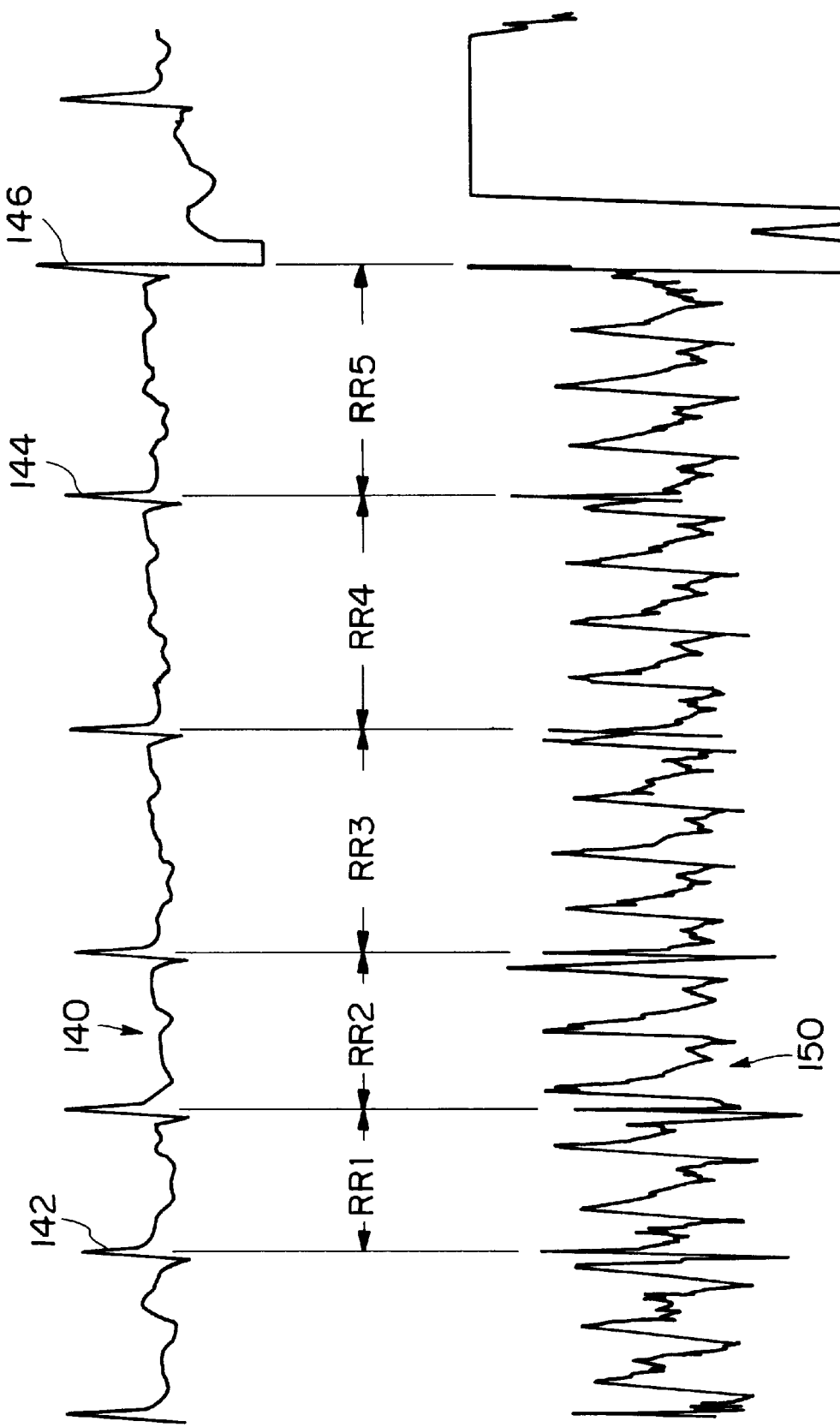
FIG. 4 is a an additional set of electrogram tracings illustrating the correlation function performed by the present invention.

FIG. 4 illustrates the operation of the correlation algorithm over a series of R—R intervals extending from R-R-1 to R-R-5. The illustrated tracings include an electrogram 140, corresponding to the output of amplifier 200 in FIG. 2 and a second electrogram 150, corresponding to the output of the wide band amplifier 210 in FIG. 2. Prior to R wave 142, the high voltage charging circuit has finished charging the output capacitors and is ready to deliver an atrial defibrillation pulse. At this point, digitization of the electrocardiogram signal from amplifier 210 begins, resulting in successively stored electrocardiogram segments corresponding to R-R-1, R-R-2, R-R-3, R-R-4 and R-R-5. In the specific embodiment described herein, the correlation between the electrograms stored during each R—R interval and the preceding R—R interval takes place following the R wave ending the R—R interval. However, the corellation analysis might also be performed upon completion of storage of the electrogram segment, prior to occurrence of the R-wave ending the R—R interval. Because the correlation between the electrograms stored in R-R-1 and R-R-2 and the correlation between the electrograms stored in R-R-2 and R-R-3 are not sufficiently great to exceed the defined correlation threshold. However, following R wave 144, microprocessor 224 determines that the correlation between the electrogram signals corresponding to R-R-3 and R-R-4 does exceed the correlation threshold, triggering delivery of an atrial defibrillation pulse, synchronized to the next occurring R wave 146. In a device as illustrated it is assumed that given the relatively slow clock rates of microprocessors in implantable defibrillators today, the process of performing the correlation analysis will extend for a period of time which prevents delivery of the defibrillation pulse synchronized with R-wave 144. However, as development of these types of devices advances, it is anticipated that the correlation analysis may be completed in time to deliver the defibrillation pulse synchronized to the R-wave ending the second of the R—R intervals employed in the correlation analysis.

The same correlation function may also be applied over a series of intervals in conjunction with the initial detection of an atrial tachyarrhythmia as discussed below, with a record kept of how many successive R—R intervals exhibited the desired degree of correlation with the preceding R—R intervals or a record of how many of the preceding series of R—R intervals had a sufficiently high correlation with the preceding R—R intervals. This value may be employed as part of a detection algorithm to distinguish between atrial defibrillation and atrial flutter, as discussed in more detail below in conjunction with FIG. 5.

Figure 5:
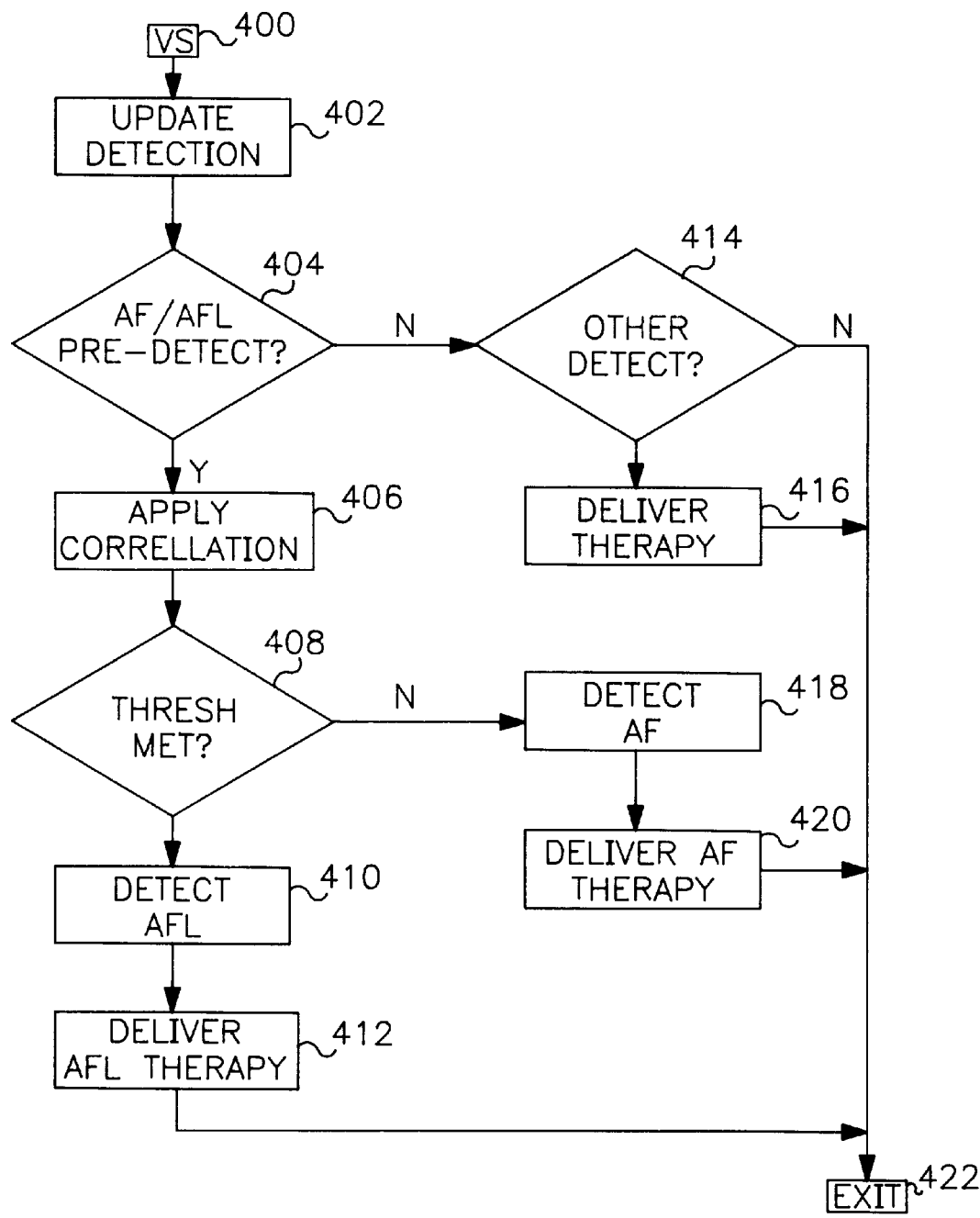
FIG. 5 is a functional flow chart illustrating a first implementation of the present invention.

FIG. 5 is a functional flow chart illustrating the overall operation of the correlation function as part of an arrhythmia detection system included in an implantable arrhythmia device as described above. In response to a sensed ventricular depolarization at 400, the microprocessor 224 (FIG. 2) updates all of the ongoing detection criteria at 402 to determine whether it has detected an arrhythmia. If the microprocessor detects an atrial rhythm which may be atrial defibrillation or a flutter at 404, using any of the known algorithms for atrial fibrillation and atrial flutter detection, the correlation finction is applied at 406, if the length of R—R intervals permits storage of an electrogram segment persisting for the desired number of A—A intervals. If either of the R—R intervals is too short to permit storage of an electrogram segment of the desired length, the correlation threshold is determined not to be met. The correlation function may be applied to electrograms stored during R—R intervals occurring after or before the criteria indicating the likely occurrence of a high rate atrial tachyarrhythmia at 404 are met. At 408, the microprocessor determines whether the correlation threshold has been met. The correlation threshold may be considered to have been met in response to a sequence of a predetermined number, e.g. 2, 3 or 4 of electrogram segments stored during succeeding R—R intervals which exhibit the required degree of correlation, or may be considered to be met in response to the occurrence of a preset number of stored electrogram segments or a preceding series of R—R intervals, for example, five out of eight, which have the required degree of correlation to preceding R—R intervals. If the correlation threshold is met at 408, the microprocessor 224 determines that the detected rhythm is likely atrial flutter or highly organized atrial fibrillation at 410, and delivers the therapy scheduled in such circumstances at 412. In the event that the correlation threshold is not met at 408, the microprocessor 224 determines that the high rate atrial arrhythmia is in fact atrial fibrillation and triggers delivery of the scheduled atrial fibrillation therapy at 420, typically a high voltage defibrillation pulse.

If the microprocessor 224 detects an arrhythmia other than a high rate atrial tachyarrhythmia at 414, it correspondingly triggers delivery of the scheduled therapy at 416, and returns to normal operation at 422.

Figure 6:
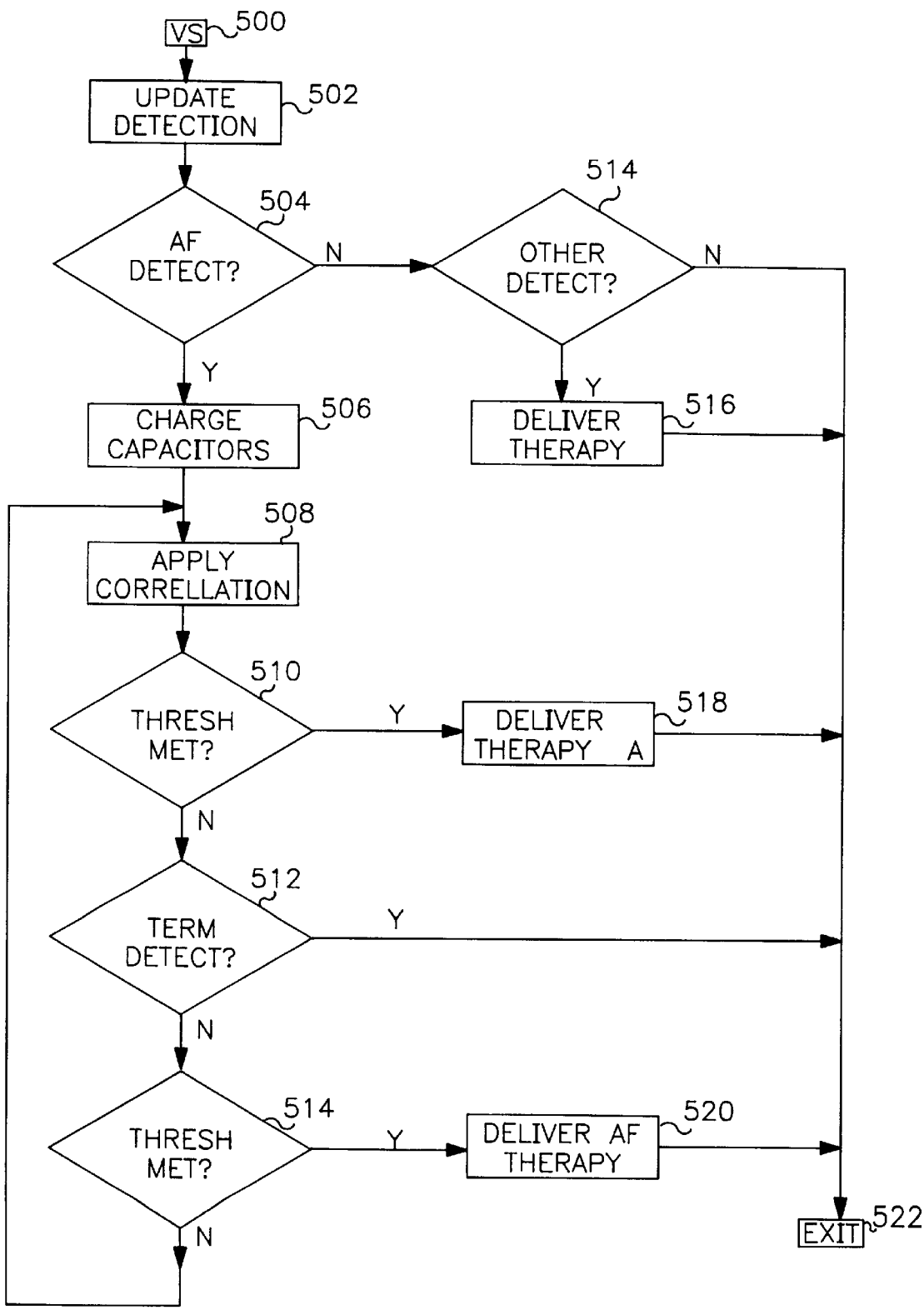
FIG. 6 is a functional flow charge illustrating a second implementation of the present invention.

In conjunction with the functional flow chart illustrated in FIG. 5, it should be understood that the process of delivering the scheduled atrial fibrillation or atrial flutter therapy may itself involve a second application of the correlation function, corresponding to that illustrated in FIG. 6. Alternatively, application of the correlation function as in FIG. 6 may occur following a preliminary detection of a high rate atrial tachyarrhythmia without previous application of the correlation function.

FIG. 6 illustrates application of the correlation function after an initial detection of a high rate atrial arrhythmia consistent with atrial fibrillation and/or atrial flutter. In this embodiment of the invention the correlation function may be employed to determine the timing of the delivery of a cardioversion/defibrillation pulse scheduled as a therapy and, or may be employed to select between two therapies of different aggressiveness. Following any sensed ventricular depolarization at 500, the microprocessor 224 updates its detection mechanisms and determines at 504 whether atrial fibrillation or other high rate atrial tachyarrhythmia is present. This step may correspond to step 418 of FIG. 5, in some embodiments of the invention. If atrial fibrillation is determined to be present, the output capacitors are charged at 506, if the first scheduled Therapy A is a cardioversion/defibrillation pulse, and the correlation function is applied at 508 either during or after charging of the high voltage capacitors, if the capacitors are to be charged, the corellation function determining the correlation of the electrograms stored corresponding to each R—R interval to the previous stored electrogram segment, if the lengths of R—R intervals permits storage of electrogram segments persisting for the desired number of A—A intervals. If either of the R—R intervals is too short to permit storage of an electrogram segment of the desired length, the correlation threshold is determined not to be met. In response to a predetermined number, e.g. two successive stored electrocardiogram segments meeting a defined level of correlation at 510, the microprocessor 224 determines that the high rate atrial arrhythmia is either atrial flutter or relatively more organized atrial fibrillation, and triggers delivery of a the first scheduled Therapy A at 518. If this scheduled therapy is a cardioversion or defibrillation pulse, and the application of the correlation functioning in this circumstance assists in delivering the cardioversion or defibrillation pulse at a time at which the threshold for conversion of the arrhythmia to a normal sinus rhythm is likely to be at its lowest level. Alternatively, the first scheduled therapy may be a lower energy therapy such as a pacing level pulse burst as described above.

In the event that the electrogram stored during the most recent R—R interval does not exhibit a required degree of correlation to the preceding stored electrogram segment, the microprocessor checks at 512 to determine whether the arrhythmia is terminated. If so, the device returns to normal operation. If termination is not detected, the microprocessor 224 checks at 514 to determine whether a defined time interval or number of R—R intervals has expired since either charge up of the high voltage capacitors at 506 or detection of the high rate atrial arrhythmia at 504. If the interval has expired, the microprocessor 224 triggers delivery of a set scheduled therapy B at 520. Therapy B may be the same as Therapy A at 518, in which case, application of the correlation functions merely serves to determine the time of delivery of the therapy. Optionally, Therapy B delivered at 520 may be a different therapy from Therapy A, for example, a higher amplitude cardioversion or defibrillation pulse reflective of the fact that the high rate atrial arrhythmia under way is less organized, and thus less likely to have a higher threshold for conversion to sinus rhythm. If Therapy A is a pacing pulse level therapy, such as a burst pacing pulse therapy as described above Therapy B may be a high amplitude cardioversion or defibrillation, reflecting the fact that a relatively more organized atrial fibrillation or atrial flutter is more likely to be terminated if a pacing pulse therapy than is a relatively less organized atrial fibrillation. Charging or additional charging of the high voltage output capacitors may this be a part of the therapy delivery step 520. Synchronization of any delivered atrial cardioversion pulse is of course included in both therapy delivery steps 518 and 520. In the event that an arrhythmia other than atrial fibrillation is detected at 514, the therapy scheduled for that arrhythmia is delivered at 516 and the device returns to normal operation at 522.

In conjunction with FIG. 6 it should be understood that the step 504 of the detection of an atrial tachyarrhythmia which may be fibrillation may in fact correspond to the detection of atrial fibrillation at 418, illustrated in FIG. 5, with steps 506, 508, 510, 518, 512, 514 and 520 corresponding generally to the single functional block 420, illustrated in FIG. 5. In this fashion, a detection and synchronization mechanism is provided which employs the measurement of electrogram correlation twice, once for initial detection, once for control of the timing and optional nature of the delivered therapy.

In conjunction with the flow charts of both FIGS. 5 and 6, if the invention is embodied in a prioritized rule based detection system as described in the above cited Gillberg et al. patent application or as and disclosed in the above-cited Olson et al patent, detection of a rhythm consistent with atrial fibrillation or flutter at 404 or 410 in FIG. 5 and at 504 in FIG. 6 should be understood to be subject to the requirement that no other higher priority rule for detection of a tachyarrhythmia is met concurrently. In contrast, if the invention is embodied in the context of devices in which only one arrhythmia detection rule can be met at any one time, detection of atrial fibrillation or flutter should be understood to be mutually exclusive to detection of other arrhythmias in conjunction with FIGS. 5 and 6.

It is most likely that commercial embodiments of a device embodying the present invention will require the use of a microprocessor in order to perform the numerous calculations anthat lysis steps required, it is within the realm of possibility that some or all of the detection criteria provided by the microprocessor in the above disclosure might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties. Thus, the above description should be considered exemplary, rather than limiting, with regard to the interpretation of the following claims.

In conjunction with the above disclosure, we claim:

1. In an implantable medical device having means for sensing atrial electrograms, means for detecting atrial tachyarrhythmias and an atrial cardioversion/defibrillation pulse generator, the improvement wherein:

said device includes an electrogram recorder means for storing atrial electrogram segments, a correlator measuring correlation successive stored atrial electrogram segments and means for defining a required degree of correlation; and wherein the atrial cardioversion/defibrillation pulse generator generates a cardioversion/defibrillation pulse responsive to a measured correlation of stored electrogram segments of at least the defined degree of correlation following detection of an atrial tachyarrhythmia.

2. In an implantable medical device having means for sensing atrial electrograms, means for detecting atrial tachyarrhythmias and means for delivering first, less aggressive and second, more aggressive anti-atrial arrhythmia therapies in response to detection of atrial tachyarrhythmias, the improvement wherein:

said device includes an electrogram recorder for storing atrial electrogram segments, a correlator measuring correlation successive stored atrial electrogram segments and means for defining a required degree of correlation; and wherein the therapy means delivers a first, less aggressive therapy responsive to a measured correlation of stored electrogram segments of at least the defined degree of correlation following detection of an atrial tachyarrhythmia.

3. In an implantable medical device having means for sensing atrial electrograms, means for detecting first and second atrial tachyarrhythmias and means for delivering anti-atrial arrhythmia therapies in response to detection of atrial tachyarrhythmias, the improvement wherein:

said device includes an electrogram recorder for storing atrial electrogram segments, a correlator measuring correlation successive stored atrial electrogram segments and means for defining a required degree of correlation; and wherein the detection means detects said first atrial tachyarrhythmia responsive to a measured correlation of stored electrogram segments of at least the defined degree of correlation.

4. A device according to claim 1 or claim 2 or claim 3 wherein said electrogram recorder comprises a means for storing electrogram segments associated with successive R—R intervals.

5. A device according to claim 4 wherein said electrogram recorder comprises a means for storing electrogram segments associated with successive R—R intervals which extend over multiple atrial depolarizations.

6. A device according to claim 5 wherein said electrogram recorder comprises a means for storing electrogram segments which extend over intervals less than their associated R—R intervals.

7. A device according to claim 5 wherein said electrogram recorder comprises a means for storing electrogram segments which extend over intervals less than their associated R—R intervals.

8. A device according to claim 1 or claim 2 or claim 3 wherein said correlator comprises means for shifting said stored electrogram segment relative to one another until a maximum corellation is obtained and wherein said detection means detects said first atrial tachyarrhyththmia responsive to said maximum correlation of stored electrogram segments having at least the defined degree of correlation.

9. A device according to claim 8 wherein said electrogram recorder comprises a means for storing electrogram segments associated with successive R—R intervals.

10. A device according to claim 9 wherein said electrogram recorder comprises a means for storing electrogram segments associated with successive R—R intervals which extend over multiple atrial depolarizations.

* * * * *